(12) United States Patent
Lee et al.

(10) Patent No.: US 6,346,257 B1
(45) Date of Patent: Feb. 12, 2002

(54) PROCESS FOR PREPARING WATER-IN-OIL TYPE EMULSION COSMETIC COMPOSITION CONTAINING L-ASCORBIC ACID WITH IMPROVED STABILITY

(75) Inventors: Hun Jin Lee, Chonan; Jeoung Woung Hwang, Osan; Yong Joon Cha, Whasung-Gun, all of (KR)

(73) Assignees: Skinplus Co., LTD, Seoul; Cosmax Co., Ltd., Kyunggi-Do, both of (KR)

( * ) Notice: Subject to any disclaimer, the term of this patent is extended or adjusted under 35 U.S.C. 154(b) by 0 days.

(21) Appl. No.: 09/433,746

(22) Filed: Nov. 4, 1999

(30) Foreign Application Priority Data

Dec. 9, 1998 (KR) .............................................. 98-53973

(51) Int. Cl.⁷ ................................................. A61K 7/00
(52) U.S. Cl. ........................................ 424/401; 514/474
(58) Field of Search ........................... 424/401; 514/474

(56) References Cited

FOREIGN PATENT DOCUMENTS

JP 08133958 * 5/1996

\* cited by examiner

Primary Examiner—S. Mark Clardy
Assistant Examiner—Michael A. Williamson
(74) Attorney, Agent, or Firm—McDermott, Will & Emery

(57) ABSTRACT

Disclosed is a process for preparing water-in-oil type emulsion cosmetic compositions containing L-ascorbic acid. The use of 2-hydroxypropyl cyclodextrin and a water-in-oil type emulsion allow L-ascorbic acid itself to be preserved for a lengthy period of time with high functional maintenance. Even after being stored for a significant period of time, the water-in-oil type emulsion cosmetic compositions do not exhibit discoloration nor give out offensive odor nor show the separation of cosmetic ingredients. In addition, the cosmetic compositions keep L-ascorbic acid high in the effective whitening activity, such as melanin reduction and inhibitory activity against tyrosinase.

2 Claims, No Drawings

PROCESS FOR PREPARING WATER-IN-OIL TYPE EMULSION COSMETIC COMPOSITION CONTAINING L-ASCORBIC ACID WITH IMPROVED STABILITY

BACKGROUND OF THE INVENTION

1. Field of the invention

The present invention relates, in general, to a process for preparing water-in-oil type emulsion cosmetic compositions containing L-ascorbic acid and, more particularly, to an improvement in the stability in cosmetic compositions and the whitening activity of L-ascorbic acid, along with the process.

2. Description of the Prior Art

In recent years, active research has been directed to the development of cosmetic whitening agents and whitening cosmetics. Particularly, the whitening cosmetic market of Asia has yearly increasingly explosive growth.

The mechanism of whitening agents is largely believed to follow one of the following three courses:

(1) melanin reduction and depigmentation;

(2) inhibition against tyrosinase activity; and (3) control of cytokine network.

Oxidized melanin shows dark colors. When being reduced, melanin is decolorized to pale yellow. Well known as melanin reducing agents are vitamins, including tocopherol, L-ascorbic acid, and derivatives thereof. Of them, L-ascorbic acid draws great attention because it is found to have an inhibitory activity against tyrosinase in addition to showing depigmentation. Further, with a high degree of safety to the human body, L-ascorbic acid is used as a thermally useful material in a broad spectrum of cosmetics.

L-ascorbic acid, however, suffers from a disadvantage of being easily oxidized and degraded by moisture or acid. That is, when brought into contact with moisture or acid, L-ascorbic acid loses its effective activity as well as causes yellowing and gives out an offensive odor.

Accordingly, stabilization of L-ascorbic acid has been a hot issue in the art. As a consequence of continual research, various L-ascorbic acid derivatives, which are stable to acid and moisture, and protective systems such as liposomes are developed. In detail, Japanese Pat. Laid-Open Publication No. Heisei 2-83309 discloses a water-in-oil type emulsion which contains water-soluble L-ascorbic acid derivatives in its inner phase so as to protect them from oxidation and degradation. Japanese Pat. Laid-Open Publication No. Showa 55-64511 suggests an inclusion of higher fatty acid esters of L-ascorbic acid in cyclodextrin. Japanese Pat. Laid-Open Publication No. Heisei 3-5426 introduces a liposome concept in improving the preservatory stability of L-ascorbic acid, teaching that L-ascorbic acid phosphate or sulfate is added in a liposome. In Japanese Pat. Laid-Open Publication No. Heisei 5-345714, there are disclosed certain water-soluble polymers which can be formulated with inorganic acid ester of L-ascorbic acid.

All of the above-cited references utilize ester derivatives of L-ascorbic acid. Improved as they are in stability compared with L-ascorbic acid itself, the L-ascorbic acid derivatives are found to show poor melanin reduction or minute inhibitory activity against tyrosinase.

SUMMARY OF THE INVENTION

The intensive and thorough research on the use of L-ascorbic acid in cosmetics, repeated by the present inventors aiming to improve the stability as well as the functionality of L-ascorbic acid, resulted in the finding that the use of 2-hydroxypropyl cyclodextrin and a water-in-oil type emulsion allow L-ascorbic acid itself to be preserved for a lengthy period of time with high functional maintenance.

Therefore, it is an object of the present invention to overcome the above problems encountered in prior arts and to provide a water-in-oil type emulsion cosmetic composition containing L-ascorbic acid, which can preserve L-ascorbic acid itself for a lengthy period of time as well as keep the function of L-ascorbic acid high.

It is another object of the present invention to provide a method for preparing such an L-ascorbic acid-containing, water-in-oil type emulsion cosmetic composition.

In an embodiment of the present invention, a water-in-oil type emulsion cosmetic composition containing L-ascorbic acid with improved stability is prepared according to a method comprising the steps of: (1) formulating L-ascorbic acid at an amount of 1–8 weight % with a 1:1 mix of 2-hydroxypropyl cyclodextrin and pure water while stirring at room temperature for 12 hours or longer to give an L-ascorbic acid base composition; (2) admixing the L-ascorbic acid base composition with a water-soluble component comprising 10–60 weight % of polyol to give an aqueous phase system; (3) mixing 2–4 weight % of a block-copolymeric non-ionic surfactant, 1–2 weight % of an ordinary non-ionic surfactant and 1–5 weight % of polyoxyethylene methylpolysiloxane at 65–75° C. to produce an emulsion composition; (4) admixing 10–20 weight % of hydrocarbon oil with the emulsion composition to give an oil-phase system; and (5) mixing the aqueous phase system with the oil-phase system with stirring. In an aspect of the present invention, the 2-hydroxypropyl cyclodextrin is used at an amount of 5–25 weight % based on the weight of the water-in-oil type emulsion cosmetic composition.

DETAILED DESCRIPTION OF THE INVENTION

The present invention is characterized in that an L-ascorbic acid base formulation comprising 1–8 weight % of L-ascorbic acid and a mixture of 1:1 2-hydroxypropyl cyclodextrin and pure water is admixed with an aqueous phase component composition and then with an oil-phase component composition.

The aqueous phase component comprises 10–60 weight % of polyol based on the weight of the water-in-oil type emulsion cosmetic composition.

In the water-in-oil type emulsion cosmetic composition, 2-hydroxypropyl cyclodextrin amounts to 5–25 weight % and pure water is added to a final volume of 100 weight %.

As for the oil-phase component composition, it comprises 2–4 weight % of a block-copolymeric non-ionic surfactant, 1–2 weight % of an ordinary non-ionic surfactant, 1–5 weight % of a polyoxyethylene methylpolysiloxane copolymer, and 10–20 weight % of a hydrocarbon oil, based on the weight of the water-in-oil type emulsion cosmetic composition. To prepare the oil-phase component composition, a block-copolymeric non-ionic surfactant, an ordinary non-ionic surfactant, and polyoxyethyelene methyl polysiloxane are first mixed together at predetermined amounts at 65–75° C. and then, with a hydrocarbon oil.

The block co-polymeric non-ionic surfactant has both a hydrophilic group and a hydrophobic group in its molecular structure, exemplified by polyethylene glycol (PEG)-30 dipolyhydroxy stearate. Useful as the ordinary non-ionic surfactant is polyglyceryl-2-diisostearate. With regard to the hydrocarbon oil, it may be selected from those that are usually used in water-in-oil type emulsion cosmetic compositions. Examples of useful hydrocarbon oil include squalene and cetyl octanoate.

In accordance with the present invention, L-ascorbic acid is formulated with a mix of 1:1 2-hydroxypropyl cyclodextrin and pure water and the resulting formulation is stirred at room temperature for 12 hours. This separate L-ascorbic acid base formulation assures the L-ascorbic acid of stability in the water-in-oil type emulsion cosmetic composition.

Even after being stored for a significant period of time, the water-in-oil type emulsion cosmetic composition of the present invention does not exhibit discoloration nor gives out offensive odor nor shows the separation of cosmetic ingredients. In addition, the cosmetic composition of the present invention keeps L-ascorbic acid high in the effective whitening activity, such as melanin reduction and inhibitory activity against tyrosinase.

A better understanding of the present invention may be obtained in light of the following examples which are set forth to illustrate, but are not to be construed to limit the present invention.

EXAMPLES I

In a mix of 5 weight % of 2-hydroxypropyl cyclodextrin and 5 weight % of pure water was added 1 weight % of L-ascorbic acid, followed by stirring the mixture at room temperature for about 12 hours to give an L-ascorbic acid base composition.

Next, 40 weight % of propylene glycol, 20 weight % of glycerin, 0.3 weight of rosin, and 0.7 weight % of magnesium sulfate were well dissolved in 6 weight % of pure water, and mixed with the L-ascorbic acid base composition to give an aqueous phase system.

Separately, a mixture comprising 1 weight % of polyethylene glycol-30 dipolyhydroxy stearate, 1 weight % of polyglyceryl-2-diisostearate, 3 weight % of polyoxyethylene methylpolysiloxane, 5 weight % of cyclomethycon, 1 weight % of dimethycon, 5 weight % of cetyl octanoate, 5 weight % of squalene, 0.5 weight of a preservative, and 0.5 weight % of bentonite was melted by heating at 65–70° C., and cooled to 40° C. to give an oil-phase system.

Thereafter, the oil-phase system was slowly added with the aqueous phase system while being stirred at 2,000 rpm by use of a homo mixer. During the addition, the rpm of the homo mixer was increased when the viscosity increased. After completion of the addition, the resulting mixture was further stirred at 3,500 rpm for 70 min by use of a homo mixer and cooled to prepare a water-in-oil type emulsion cosmetic composition containing L-ascorbic acid.

EXAMPLES II AND III

The same procedure as in Example I was repeated except that the ingredients were used according to the indications of Table 1, below.

TABLE 1

| System | | Example Nos. | | |
|---|---|---|---|---|
| Phase | Components | 1 | 2 | 3 |
| Oil Phase | Cyclomethycon | 5.0 | 5.0 | 5.0 |
| | Polyoxyethylenemethyl polysiloxane | 3.0 | 3.0 | 3.0 |
| | PEG-30 dipolyhydroxy stearate | 1.0 | 1.0 | 4.0 |
| | Polyglyceryl-2-diisosterarate | 1.0 | 1.0 | 2.0 |
| | Dimethycon | 1.0 | 1.0 | 2.0 |
| | Squalene | 5.0 | 5.0 | 5.0 |
| | Cetyl octanoate | 5.0 | 5.0 | 5.0 |
| | Preservative | 0.5 | 0.5 | 0.5 |
| | Bentonite | 0.5 | 0.5 | 0.5 |
| Aqueous Phase | L-Ascorbic acid | 1.0 | 5.0 | 8.0 |
| | 2-Hydroxypropyl cyclodextrin | 5.0 | 15.0 | 25.0 |
| | Rosin | 0.3 | 0.3 | 0.3 |
| | Propylene glycol | 40.0 | 30.0 | 5.0 |
| | Glycerin | 20.0 | 5.0 | 5.0 |
| | Magnesium sulfate | 0.7 | 0.7 | 0.7 |
| | Pure water | to 100 | to 100 | to 100 |

COMPARATIVE EXAMPLE I

An oil-phase system was prepared by heating a mixture comprising oil-phase components as shown in Table 2, below, at 70° C. and cooled. Separately, an aqueous-phase system was prepared by heating a mixture comprising water-soluble components as shown in Table 2, at 70° C. The aqueous phase system was added in the oil-phase system, followed by stirring by use of a homo mixer to give a water-in-oil type emulsion cosmetic composition.

COMPARATIVE EXAMPLE II

According to the indication of Table 2, below, L-ascorbic acid was mixed with β-cyclodextrin and then with the remaining water-soluble components at 70° C. and cooled. Thereafter, this resulting aqueous phase system was added in an oil-phase system which was prepared as in Comparative Example I.

COMPARATIVE EXAMPLE III

A water-in-oil type emulsion cosmetic composition was prepared in a similar manner to that of Comparative Example I, except that a 10% L-ascorbic acid-containing liposome was used instead of L-ascorbic acid, as indicated Table 2, below.

TABLE 2

| System | | Comparative Examples | | |
|---|---|---|---|---|
| Phase | Components | 1 | 2 | 3 |
| Oil Phase | Cyclomethycon | 5.0 | 5.0 | 5.0 |
| | Polyoxyethylenemethyl polysiloxane | 3.0 | 3.0 | 3.0 |
| | PEG-30 dipolyhydroxy stearate | — | — | — |
| | Polyglyceryl-2-diisosterarate | 2.0 | 2.0 | 2.0 |
| | Dimethycon | 1.0 | 1.0 | 1.0 |
| | Squalene | 5.0 | 5.0 | 5.0 |
| | Cetyl octanoate | 5.0 | 5.0 | 5.0 |
| | Preservative | 0.5 | 0.5 | 0.5 |
| | Bentonite | 0.5 | 0.5 | 0.5 |
| Aqueous Phase | L-Ascorbic acid | 5.0 | 5.0 | — |
| | β-Cyclodextrin | — | 5.0 | — |
| | Liposome with 10% Ascorbic Acid | — | — | 50.0 |
| | Rosin | 0.3 | 0.3 | 0.3 |
| | Propylene glycol | 40.0 | 40.0 | 5.0 |
| | Glycerin | 20.0 | 20.0 | 5.0 |
| | Magnesium sulfate | 0.7 | 0.7 | 0.7 |
| | Pure water | to 100 | to 100 | to 100 |

TEST EXAMPLE I

Long-Term Preservatory Safety

The water-in-oil type emulsion cosmetic compositions prepared in Examples and Comparative Examples were assayed for long-term preservatory safety as they were or while being contained in airtight tubes. Assaying was conducted at room temperature and in an incubator whose temperature was maintained at 0° C. and 40° C. and cycled between these temperatures. The results are given in Table 3, below.

TABLE 3

| Storage States and Period of Cosmetic Compositions | | | Examples | | | C. Examples | | |
|---|---|---|---|---|---|---|---|---|
| | | | 1 | 2 | 3 | 1 | 2 | 3 |
| 0° C. | Naked | 1 week | o | o | o | o ◇ | o ◇ | o ◇ |
| | | 1 month | o | o | o | o | x | x |
| | | 6 months | o | o | o | x | x | x |
| | In tube | 1 week | o | o | o | Δ | Δ | Δ |
| | | 1 month | o | o | o | x | x | x |
| | | 6 months | o | o | o | x | x | x |
| 40° C. | Naked | 1 week | o | o | o | Δ ◇ | Δ ◇ | Δ ◇ |
| | | 1 month | o | o | o | x | x | x |
| | | 6 months | o ◇ | o ◇ | o ◇ | x | x | x |
| | In tube | 1 week | o | o | o | Δ | Δ | Δ |
| | | 1 month | o | o | o | x | x | x |
| | | 6 months | o | o | o | x | x | x |
| Cycle | Naked | 1 week | o | o | o | Δ ◇ | Δ ◇ | Δ ◇ |
| | | 1 month | o | o | o | x | x | x |
| | | 6 months | o | o | o | x | x | x |
| | In tube | 1 week | o | o | o | Δ | Δ | Δ |
| | | 1 month | o | o | o | Δ | Δ | Δ |
| | | 6 months | o | o | o | x | x | x |
| RT | Naked | 1 week | o | o | o | o ◇ | o ◇ | o ◇ |
| | | 1 month | o | o | o | Δ | Δ | Δ |
| | | 6 months | o | o | o | x | x | x |
| | In tube | 1 week | o | o | o | o | o | o |
| | | 1 month | o | o | o | x | x | x |
| | | 6 months | o | o | o | x | x | x | o stable cosmetic formulation
Δ unstable cosmetic formulation
◇ separated cosmetic formulation
x discolored and stink

TEST EXAMPLE II

While being stored in an incubator maintained at 40° C., water-in-oil type emulsion cosmetic compositions prepared in Examples II and III and Comparative Examples I to III were measured for L-ascorbic acid content at predetermined time periods. Percent of retention of L-ascorbic acid was calculated and the results are given in Table 2, below.

Test Method
(1) Preparation of Sample Solutions 0.1 g of a sample was dissolved in a 20 ml flask containing methanol, and subjected to high performance liquid chromatography (HPLC) after undergoing standardization.
(2) Preparation of Standard Solution After being dissolved in methanol in a 100 ml flask, each of 10, 20 and 30 mg of L-ascorbic acid was standardized and subjected to HPLC.
(3) HPLC Conditions Column: Hypersil ODS ($C_{18}$)

Mobile Phase: $H_2O$ 100% (pH 2.5 controlled with $H_3PO_4$)

Detection: UV 245 nm

Elution Rate: 1 ml/min

Feeding Rate: 10 $\mu l$

TABLE 4

| % Retention of L-Ascorbic acid | | | | | | |
|---|---|---|---|---|---|---|
| Examples | 1 hr | 1 day | 3 days | 7 days | 1 month | 3 months |
| 2 | 97.2 | 92.6 | 88.4 | 85.8 | 70.4 | 26.8 |
| 3 | 96.0 | 94.3 | 93.3 | 91.0 | 77.9 | 37.0 |
| C. 1 | 80.8 | 48.6 | 14.4 | 0 | 0 | 0 |
| C. 2 | 82.4 | 37.2 | 19.4 | 0 | 0 | 0 |
| C. 3 | 96.4 | 43.2 | 20.8 | 12.4 | 0 | 0 |

As apparent from the data of Table 4, the L-ascorbic acid of the compositions prepared in Examples II and III outlasts that of the compositions prepared in Comparative Examples I to III.

TEST EXAMPLE III

Assay for Primary Dermal Irritation

The water-in-oil type emulsion cosmetic compositions prepared in Examples and Comparative Examples were applied to respective pin chambers for patch tests, which were then fixed on the inner skin surfaces of the forearms of 20 healthy adults for 48 hours with the aid of tapes. At 2 hours after removal of the pin chambers, dermal irritation was evaluated under observation of the naked eye. In this regard, dermal irritation indexes were calculated according to the following equation in view of the standards of Table 5, below.

TABLE 5

| Standards for the observation of the naked eye | | | |
|---|---|---|---|
| Erythema | Sign | Note | Weighte Index |
| Negative | – | None | 0 |
| Pseudo-positive | ± | A bit more reddish than environs | 1 |

TABLE 5-continued

Standards for the observation of the naked eye

| Erythema | Sign | Note | Weighte Index |
|---|---|---|---|
| Light positive | + | Reddish over ⅓ area | 2 |
| Heavy positive | ++ | Distinctly reddish | 3 |
| Strong positive | +++ | Red blister, browned, scaly edema | 4 |

Equation 1

$$\text{Initial Degree} = \frac{\{\text{No. of } (\pm) \times 1\} + \{\text{No. of } (+) \times 2\} + \{\text{No. of } (++) \times 3\} + \{\text{No. of } (+++) \times 4\}}{\text{No. of Testees}}$$

TABLE 6

| Testee Nos. | Examples | | | Comparative Examples | | |
|---|---|---|---|---|---|---|
| | 1 | 2 | 3 | 1 | 2 | 3 |
| 1 | − | − | − | − | ± | − |
| 2 | − | ± | − | ± | − | ± |
| 3 | − | − | − | − | − | ± |
| 4 | − | − | − | − | − | − |
| 5 | ± | ± | − | ± | − | − |
| 6 | − | − | − | − | − | − |
| 7 | − | − | − | − | − | − |
| 8 | − | − | − | − | − | − |
| 9 | − | − | − | − | − | − |
| 10 | − | − | − | − | − | − |
| 11 | ± | − | − | ± | ± | ± |
| 12 | − | − | − | − | − | − |
| 13 | − | − | ± | ± | ± | ± |
| 14 | − | − | − | − | − | − |
| 15 | − | − | − | − | − | − |
| 16 | − | − | − | − | − | − |
| 17 | − | − | − | − | ± | ± |
| 18 | − | − | − | − | − | − |
| 19 | − | − | − | − | − | − |
| 20 | − | − | − | − | − | − |
| Irrit. Degree | 0.1 | 0.1 | 0.05 | 0.2 | 0.2 | 0.25 |

When the results of Table 6 are considered in view of the following criterions for judging irritation, the cosmetic compositions according to the present invention have significantly reduced irritation to the skin, compared with conventional ones.

Irritation Criteria: Draize's Judgment Value

| Irritation Degree | Judgment |
|---|---|
| 0.00~0.2 | Not irritated |
| 0.21~0.5 | Slightly irritated |
| 0.51~1.25 | Fairly irritated |
| 1.26 | Seriously irritated |

As described hereinbefore, the present invention can prepare water-in-oil type emulsion cosmetic compositions which do not give out offensive odor nor show discoloration and the separation of cosmetic ingredients, but keep L-ascorbic acid high in the effective whitening activity, such as melanin reduction and inhibitory activity against tyrosinase.

The present invention has been described in an illustrative manner, and it is to be understood that the terminology used is intended to be in the nature of descriptions rather than of limitation. Many modifications and variations of the present invention are possible in light of the above teachings. Therefore, it is to be understood that within the scope of the appended claims, the invention may be practiced otherwise than as specifically described.

What is claimed is:

1. A process for preparing water-in-oil emulsion cosmetic compositions containing L-ascorbic acid with improved stability, comprising the steps of:
   (1) formulating L-ascorbic acid at an amount of 1–8 weight % with a 1:1 mix of 2-hydroxypropyl cyclodextrin and pure water while stirring at room temperature for 12 hours or longer to give an L-ascorbic acid base composition;
   (2) admixing the L-ascorbic acid base composition with a water-soluble component comprising 10–60 weight % of polyol to give an aqueous phase system;
   (3) mixing 2–4 weight % of a block-copolymeric non-ionic surfactant, 1–2 weight % of an ordinary non-ionic surfactant and 1–5 weight % of polyoxyethylene methylpolysiloxane at 65–75° C. to produce an emulsion composition;
   (4) admixing 10–20 weight % of hydrocarbon oil with the emulsion composition to give an oil-base system; and
   (5) mixing the aqueous phase system with the oil-phase system with stirring.

2. A process as set forth in claim 1, wherein the 2-hydroxypropyl cyclodextrin is used at an amount of 5–25 weight % based on the weight of the water-in-oil emulsion cosmetic composition.

\* \* \* \* \*